United States Patent [19]
Evans et al.

[11] Patent Number: 5,755,773
[45] Date of Patent: May 26, 1998

[54] ENDOLUMINAL PROSTHETIC BIFURCATION SHUNT

[75] Inventors: Michael A Evans, Palo Alto, Calif.; Edward V. Kinney, Louisville, Ky.

[73] Assignee: Medtronic, Inc., Minneapolis, Minn.

[21] Appl. No.: 658,137

[22] Filed: Jun. 4, 1996

[51] Int. Cl.$^6$ ........................................ A61F 2/06
[52] U.S. Cl. ........................................ 623/1
[58] Field of Search ................ 623/1, 12; 606/194, 606/195

[56] References Cited

U.S. PATENT DOCUMENTS

| | | |
|---|---|---|
| 4,577,631 | 3/1986 | Kreamer . |
| 5,211,683 | 5/1993 | Maginot . |
| 5,316,023 | 5/1994 | Palmaz et al. . |
| 5,360,443 | 11/1994 | Barone et al. ............ 623/1 |
| 5,425,765 | 6/1995 | Tiefenbrun et al. ....... 623/12 |
| 5,456,713 | 10/1995 | Chuter .................... 623/1 |
| 5,489,295 | 2/1996 | Piplani et al. ............ 623/1 |

FOREIGN PATENT DOCUMENTS

| | | |
|---|---|---|
| WO 95/16406 | 6/1995 | WIPO . |
| WO 95/21592 | 8/1995 | WIPO . |
| WO 95/34255 | 12/1995 | WIPO . |

OTHER PUBLICATIONS

Kato, Noriyuki, MD, et al. "Use of a Self-expanding Vascular Occluder for Embolization during Endovascular Aortic Aneurysm Repair". *Journal of Vascular and Interventional Radiology*, Jan.-Feb. 1997, vol. 8, No. 1, pp. 27–33.

*Primary Examiner*—Michael J. Milano
*Attorney, Agent, or Firm*—Townsend and Townsend and Crew LLP

[57] ABSTRACT

The present invention provides, methods, systems, and devices which allow a surgeon to seal off the branch port of a bifurcated endoluminal prosthesis, thereby effectively transforming the bifurcated prosthesis to a single-lumen prosthesis. Generally, the methods and devices of the present invention will be available for fallback procedures when the deployment of a bifurcated endoluminal prosthesis is found to be impracticable. By effectively sealing off the second branch port, the attending physician is able to completely isolate an aneurysm or other disease of the vasculature. Where it is necessary and/or desirable to provide fluid communication between the trunk lumen and the second branch lumen, a separate passage may be provided between the first and second branches of the body lumen system.

12 Claims, 15 Drawing Sheets

ENDOLUMINAL PROSTHETIC BIFURCATION SHUNT

BACKGROUND OF THE INVENTION

I. Field of the Invention

The present invention relates generally to tubular endoluminal prostheses, such as grafts, stents, stent-grafts, and the like. More particularly, the present invention provides methods, systems, and devices for sealing or occluding a branch of a branching endoluminal prosthesis, particularly when the branch to be sealed has been found to be incorrectly positioned, inaccessible, or otherwise detrimental to a prosthetic therapy for abdominal and other aneurysms, and for treatments of other branched body lumens.

Vascular aneurysms are the result of abnormal dilation of a blood vessel, usually resulting from disease and/or genetic predisposition, which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending into one or both of the iliac arteries.

Aortic aneurysms are most commonly treated in open surgical procedures, where the diseased vessel segment is bypassed and repaired with an artificial vascular graft. While considered to be an effective surgical technique, particularly considering the alternative of the usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients suffering from such aneurysms are often elderly and weakened from cardiovascular and other diseases, which reduces the number of eligible patients. Even for eligible patients prior to rupture, conventional aneurysm repair has a relatively high mortality rate, usually from 2 to 10%. Morbidity related to the conventional surgery includes myocardial infarction, renal failure, impotence, paralysis, and other conditions. Additionally, even with successful surgery, recovery takes several weeks and often requires a lengthy hospital stay.

In order to overcome all or some of these drawbacks, a variety of endovascular prosthesis placement techniques have been proposed for the treatment of aneurysms. Although some of these proposed techniques appear very promising, known methods and apparatus suffers from undesirable limitations in at least some aspect. Of particular relevance for the present invention, endovascular therapies for aneurysms which extend from the abdominal artery down along one or both iliac arteries, sometimes called aortoiliac aneurysms, have proven to be particularly problematic.

Endovascular therapies for aortoiliac aneurysms are complicated by the difficulty of sealing the aneurysm from the blood flow through the aorta and the first and second iliac arteries, while maintaining that blood flow to the separate branches of the vascular system. One approach which has been used to isolate such aneurysms was described by Dr. Parodi in "Endovascular Repair of Abdominal Aortic Aneurysms and Other Arterial Lesions", *J. Vasc. Surg.* 21: 549–57 (April, 1995). This "single-lumen" method involved deploying an unbranching tubular prosthesis from the healthy aorta above the aneurysm, through the aneurysm itself, and into one of the two iliac arteries, so that all blood flowing through the aorta was channelled into that single iliac. A portion of the blood is then transferred to the alternate portion of the vascular system (normally supplied by the alternate iliac) through a "femorofemoral bypass," a prosthetic vascular graft having an end-to-side anastomosis with each of the femoral arteries. Advantageously, known femorofemoral bypass procedures involve substantially less patient trauma than conventional invasive aortic aneurysm repair. The unused iliac artery is then occluded with detachable balloons or ligation.

Although this single-lumen method has proven to be fairly effective, the resulting blood flow path is somewhat less than ideal. The entire aortic blood flow must pass through a single iliac artery, and then separates downstream of the hypogastric artery into left and right femoral portions, providing a tortuous route which imposes a significant strain on the heart. Nonetheless, this procedure does have the advantages of only requiring a single healthy iliac artery for the endoluminal prosthesis to seal and anchor against, and is clearly preferable to allowing blood to continue to flow into a weak or ruptured aneurysm.

More recently, endovascular deployment of a bifurcated tubular prosthesis has been proposed as a therapy for aortoiliac aneurysms. Bifurcated prostheses generally have a trunk portion with a relatively large lumen for deployment in the aorta, and first and second branch portions with smaller branch lumens for deployment within each of the iliac arteries. The deployed trunk and branch portions preferably seal to each other and to the healthy vascular walls beyond the aneurysm to isolate the aneurysm from the bloodstream. Advantageously, the aortic blood flow enters the trunk prosthetic lumen, is separated into the two branch prosthetic lumens, and then flows into each of the iliac arteries in a path that approximates that of a normal, healthy vascular system. Unfortunately, deployment of such bifurcated prostheses across the aortoiliac junction is more complex than deployment of a single-lumen prosthesis.

A variety of minimally invasive techniques have been suggested for deployment of these bifurcated prostheses, including in situ assembly of multiple prosthetic modules, initial positioning of both prosthetic branch portions within a single iliac artery, initially deploying one of the branches folded up along the aorta, or the like. Regardless of the specific deployment procedure used, a tubular prosthesis having a lumen initially spans from the healthy portion of the aorta, through the aneurysm, and into one of the two iliac arteries, as was also true of the single-lumen prosthetic method. However, these techniques differ from the single-lumen method in that a branch port for the alternate iliac artery is disposed between the upstream and downstream ends of the tubular bifurcated prosthesis. Furthermore, proper initial deployment of the bifurcated prosthesis generally requires that the second branch port be properly oriented toward the alternate iliac.

Completing deployment of the bifurcated prosthesis generally involves positioning of the second branch portion in the alternate iliac. Oftentimes, the second branch portion is deployed through a catheter which extends from the iliac to the branch port of the bifurcated prostheses, thereby assembling the continuous bifurcated prosthetic lumen in situ. Such deployment of the second branch portion can be very straightforward, and in situ assembly of bifurcated prostheses appears to hold significant promise for many abdominal aortic aneurysm patients.

Unfortunately, bifurcated prosthetic therapies are not without their own disadvantages. Aortic aneurysms vary widely in location, size, and the distended shape of the aneurysm itself. Particularly in the advanced stages, aneurysms can also distort the aorta and iliac arteries surrounding the aneurysm, and tend to collect large amounts of thrombus. Diseased iliac arteries may be narrow due to plaque buildup, so that the remaining lumen is highly tortuous. In fact, diseased vessel tortuosity may prevent catheter or even guidewire passage. Furthermore, the precise shape and extent of the aneurysm can be very difficult to accurately determine. As a result, the accurate initial deployment of the bifurcated prosthesis, and in particular, the accurate orientation of the branch port, can be problematic. Even when the branch port is positioned as intended, it may turn out to be difficult and/or impossible to effectively deploy the second branch without rupturing the aneurysm, or without releasing the microthrombus from the distended aneurysm into the blood stream.

Once the physician completes initial deployment of a bifurcated prosthesis, but then finds that it is impossible to complete the deployment so as to seal off the aneurysm, massive surgical intervention is generally required to remove the partially deployed bifurcated prosthesis, and to install a conventional artificial graft. Hence, current minimally invasive bifurcated prosthetic therapies may be performed only after all the preparation, personnel, and equipment for convention aneurysm repair are in place. Clearly, such fallback requirements compromise the advantages of present bifurcated prosthetic therapies.

For these reasons, it would be desirable to provide improved endoluminal prosthetic methods, systems, and devices. It would be particularly desirable to provide endovascular therapies which would allow surgeons to take full advantage of the bifurcated prosthetic methods whenever possible, and to fall back to the single-lumen prosthetic methods when required by a particular patients physiology, or by the events as they actually unfold during initial deployment. It would further be desirable to provide methods and systems which would allow physicians to aggressively pursue the advantageous bifurcated prosthetic techniques, even when it is not entirely certain that those techniques will succeed, but to provide a less invasive fallback procedure if the complete deployment of the bifurcated prosthesis turns out to be impracticable.

II. Description of the Background Art

Co-pending U.S. patent application Ser. No. 08/615,697, filed Mar. 13, 1996, (Attorney Docket No. 16380-004100) the full disclosure of which is incorporated herein by reference, describes exemplary modular bifurcated prosthetic structures which are highly adaptable to a wide variety of patient physiologies. Provisional U.S. patent application Ser. No. 60/008,254, filed Dec. 1, 1995 (Attorney Docket No. 16380-003400), also incorporated herein by reference, describes bifurcated modular prosthetic structures and methods for assembling them in situ.

Dr. Parodi's article "Endovascular Repair of Abdominal Aortic Aneurysms and Other Arterial Lesions", *J. Vasc. Surg.* 21: 549–57 (1995), has been described above. U.S. Pat. No. 5,499,995 describes a device and method for blocking a body passageway by inserting an expandable frame into the passageway and expanding the frame therein. U.S. Pat. No. 5,489,295, describes an endovascular graft having a bifurcation, and a method for deploying the bifurcated graft by pulling one leg from the aorta down into an iliac.

SUMMARY OF THE INVENTION

The present invention provides methods, systems, and devices which allow a surgeon to seal at least one branch port of a bifurcated endoluminal prosthesis, thereby effectively allowing the physician to transform a deployed two-branch bifurcated prosthesis to a single-lumen tubular prosthesis. Generally, the methods and devices of the present invention will be available as fallback procedures when the complete deployment of a bifurcated endoluminal prosthesis is found to be impracticable. By effectively sealing off a branch port, the physician is able to completely isolate an aneurysm or other disease of the body lumen, thereby avoiding massively invasive conventional aneurysm repair surgery. Fluid communication between the trunk lumen and the second branch lumen of the body lumen system may be provided by a separate passage between the first and second branches of the body lumen system, for example, with known femorofemoral bypass procedures. The devices and methods of the present invention allow a physician to aggressively pursue the highly beneficial bifurcated endoluminal prosthetic therapies, but then allow the physician to fallback to an effective procedure which avoids the massive surgical intervention generally required to overcome an incomplete bifurcated prosthesis deployment.

As used herein, a "bifurcated" endoluminal prosthesis means an endoluminal prosthesis having at least two branches. Hence, trifurcated prostheses, in which a trunk lumen is in fluid communication with the lumens of each of three branches, as well as similar prostheses having four or more branches, are all encompassed by the term bifurcated prostheses. Similarly, bifurcated body lumens may also have more than two branch lumens.

In a first aspect, the present invention provides a method for repairing a bifurcated body lumen system. The body lumen system has a trunk lumen in fluid communication with first and second branch lumens at a luminal intersection. A tubular bifurcated endoluminal prosthesis is deployed within the body lumen system so that a trunk portion of the prosthesis extends into the trunk lumen, and a first branch portion of the prosthesis extends into the first branch lumen. A second branch port of the prosthesis is disposed between the trunk and branch portions. The method comprises substantially sealing this second branch port to prevent fluid communication between the prosthetic trunk lumen and the body lumen system through the second branch port. Often times, an alternative passage for fluid communication between the first branch lumen and the second branch lumen of the body lumen system will be provided. For example, when the bifurcated endoluminal prosthesis traverses an abdominal aortic aneurysm, blood flow to the alternative iliac (which would otherwise be blocked by the sealed branch port) will often be provided by a femorofemoral bypass procedure. Preferably, the sealing step comprises deploying a shunt within the bifurcated prosthesis so that the shunt extends from the trunk portion to the branch portion, and so that a membrane of the shunt substantially blocks fluid communication between the prosthetic trunk lumen and the second branch port. This membrane may seal against the lumen of the prosthesis itself, or may extend through the trunk and/or branch portions to seal directly against the surrounding body lumen, and will generally provide a smooth transition from the trunk lumen to the branch lumen of the completed prosthetic lumen system.

In a second aspect, the present invention provides a method for repairing an aneurysm of an abdominal aortic artery adjacent first and second iliac arteries, the method comprising deploying a bifurcated tubular endoluminal prosthesis within the aneurysm so that a trunk portion of the prosthesis having a trunk lumen extends into the aorta. A first branch portion of the prosthesis having a first branch lumen extends into the first iliac, while a second branch port of the prosthesis is disposed between the trunk and branch portions. A shunt is deployed within the bifurcated prostheses so that the shunt extends from the trunk lumen to the branch lumen, and so that the shunt substantially blocks fluid communication between the prosthetic trunk lumen and the second branch port of the bifurcated prosthesis.

Typically, it will be determined that the second branch port of the bifurcated prosthesis is substantially inaccessible for deployment of a second branch endoluminal prosthesis before the shunt is deployed. To allow blood to flow from the first femoral artery adjacent the first iliac to a second femoral artery adjacent the second iliac, a femorofemoral bypass will often be provided. Additionally, the second iliac between the aneurysm and the femorofemoral bypass will often be occluded to prevent blood from flowing back through that second iliac into the aneurysm.

In another aspect, the present invention provides a shunt for use with a bifurcated tubular endoluminal prosthesis, the bifurcated prosthesis having a branch lumen in fluid communication with a trunk lumen and a branch port disposed therebetween, the shunt comprising a substantially impermeable membrane and a support structure capable of affixing the impermeable membrane within the bifurcated prosthesis so that the impermeable membrane blocks fluid communication between the trunk lumen and the branch port of the bifurcated prosthesis. The shunt, however, will not substantially occlude fluid communication between the trunk lumen and the branch lumen when the membrane is affixed in place by the support structure.

Generally, the support structure comprises a radially expandable tubular body. In some cases, the tubular body comprises a perforate frame, while the membrane comprises a liner supported by the frame. Alternatively, the membrane may be formed integrally with the tubular body. Regardless, a branch end of the shunt is preferably capable of sealing radially against a surrounding lumen having a branch cross-section, while a trunk end of the shunt opposite the branch end is capable of sealing radially against a surrounding lumen having a trunk cross-section which is at least twice as large as the branch cross-section. The shunt will generally provide a gradually tapered lumenal cross-section when deployed to provide a smooth transition, and to avoid stagnation zones which would otherwise promote the formation of thrombus.

In yet another aspect, the present invention provides a system for repairing a diseased body lumen system, the repair system comprising a bifurcated tubular endoluminal prosthesis and a shunt. The bifurcated prosthesis has a trunk portion with a trunk lumen, a first branch portion having a first branch lumen, and a second branch port in fluid communication with the trunk lumen. The shunt includes a substantially impermeable membrane and a support structure capable of fixing the impermeable membrane to the bifurcated prosthesis so that the impermeable membrane blocks fluid communication between the trunk lumen and the second branch port of the bifurcated prosthesis. Optionally, the repair system will further comprise a branch tubular prosthesis having an end which sealingly engages the branch port of the bifurcated prosthesis when expanded therein. This branch prosthesis will typically be used as a preferred alternative to the shunt, the shunt providing a fallback only in the case that deployment of the branch prosthesis proves to be impracticable or ineffective.

DESCRIPTION OF THE SPECIFIC EMBODIMENTS

The present invention provides methods and systems which make use of radially expansible tubular prostheses, particularly grafts, stents, and stent-grafts. The methods, systems, and prostheses of the present invention are suitable for a wide variety of therapeutic uses, including stenting of bifurcated body lumens such as the bronchi, trachea, carotid, and the like. The structures and methods of the present invention will find their most immediate use as endovascular prostheses for the treatment of diseases of the vasculature, particularly aneurysms, stenoses, and the like. These prosthetic methods will generally make use of structures which are radially expansible from a narrow diameter configuration (to facilitate introduction into the body lumen) to a larger diameter deployed configuration when deployed.

Figure 1:
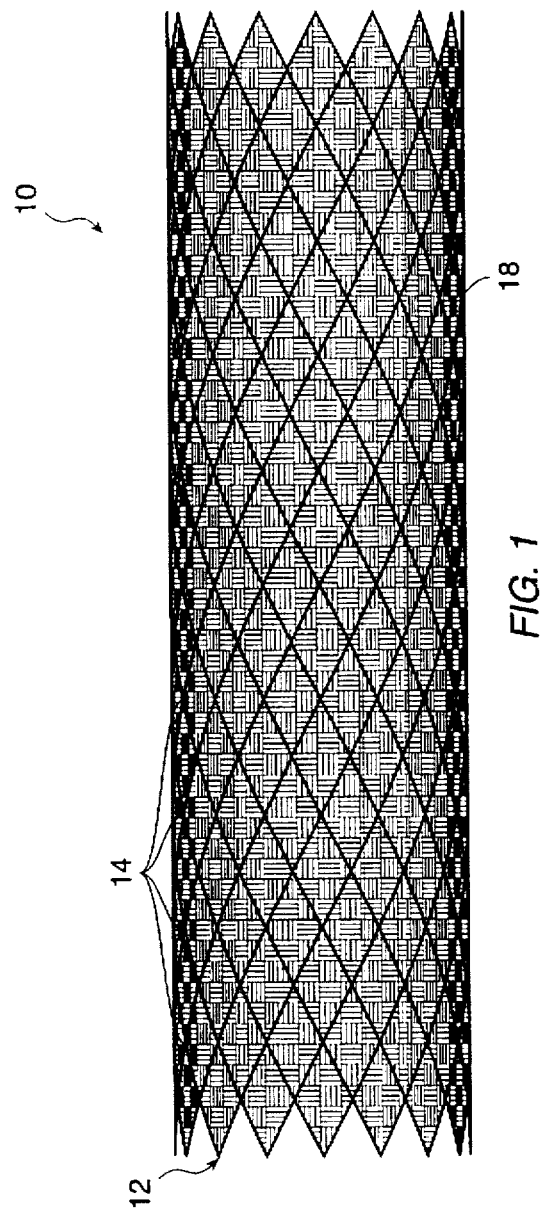
FIG. 1 is a side view of an exemplary cylindrical vascular stent-graft.

An exemplary cylindrical graft structure 10 is illustrated in FIG. 1. Prosthesis 10 comprises a preferred tubular frame 12 which includes a plurality of independent (non-connected) ring frames 14. The tubular frame 12 supports an inner liner 18. Optionally, an outer liner is disposed over the ring frames, either inside of inner liner 18, or in combination therewith.

To secure ring frames 14 in place, and to secure the liner to the preferred tubular frame 12, the liner is typically sutured to the frame. A wide variety of alternative liner frame attachment mechanisms are available, including adhesive bonding, heat welding, ultrasonic welding, and the like. Where inner and outer liners are used, the ring frames may be sandwiched between the liners and held in place by attaching the liners to each other. Alternative stent-graft structures are more fully described in U.S. application Ser. No. 08/538,706, filed Oct. 3, 1995 (Attorney Docket No. 16380-003800), the full disclosure of which is hereby incorporated by reference.

Figure 2:
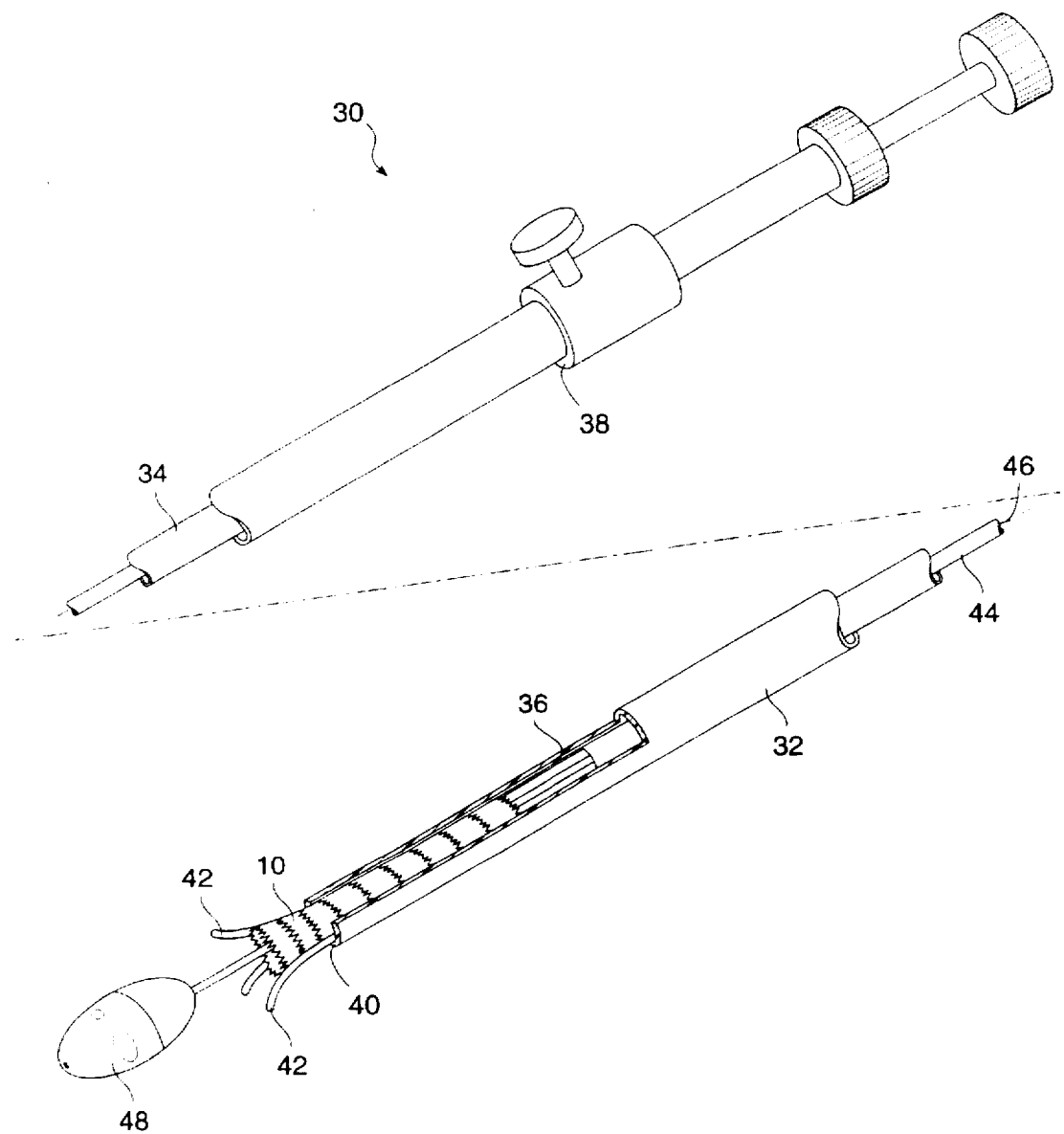
FIG. 2 is a prospective view of an exemplary delivery catheter for use with the prostheses of the present invention, with a portion of the distal end broken away to disclose a prosthesis therein.

Referring now to FIG. 2, an exemplary delivery catheter 30 for use with the endoluminal methods and systems of the present invention comprises a tubular cover 32 and a shaft 34. Cover 32 has a central lumen 36 extending from a proximal end 38 to a distal end 40. Shaft 34 is slidably received within central lumen 36 and extends proximally of cover 32. A plurality of axial runners 42 extend distally from shaft 34. Runners 42 line a portion of the inner surface of lumen 36, and slide within the lumen of the shaft. Shaft 34 also has a lumen, in which a core shaft 44 is slidably disposed. Core shaft 44 has a guidewire lumen 46, while nosecone 48 is fixed to the distal end of core shaft 44, allowing the nosecone to be manipulated independently of runners 42.

Runners 42 are generally formed from a material which is harder than the surrounding catheter body, and thereby distribute the expansion load of prosthesis 10 over the inner surface of central lumen 36. Exemplary methods and devices for prosthetic deployment are more fully described in co-pending U.S. patent application Ser. No. 08/475,200, filed Jun. 7, 1995 (Attorney Docket No. 16380-001130), the full disclosure of which is also incorporated herein by reference.

Figure 3:
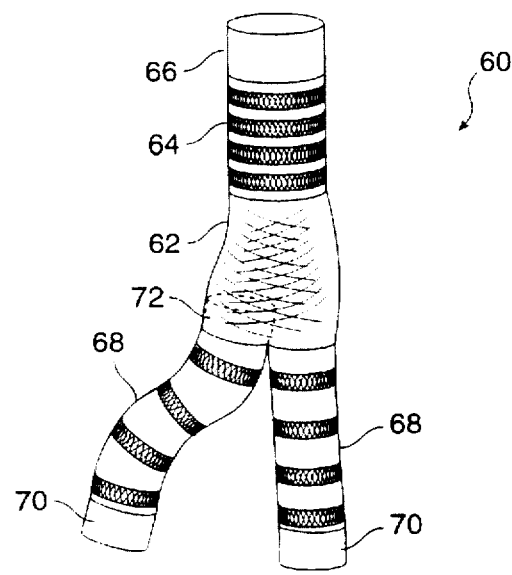
FIG. 3 illustrates an exemplary bifurcated endovascular prosthesis having a relatively rigid expanded Y-connector portion, axially flexible branch and trunk portions, and sealing/anchoring cuffs, thereby allowing the bifurcated prosthetic structure to adapt to widely varying luminal geometries.

Referring now to FIG. 3, an exemplary bifurcated endovascular prosthesis 60 comprises a lumen separation portion 62 between a trunk portion 64 and two branch portions 68. Lumen separation portion 62 preferably comprises a relatively rigid structure, while trunk portion 64 and branch portions 68 preferably provide a relatively high axial flexibility. Trunk sealing cuff 66 and branch sealing cuffs 70 securely anchor and seal the prosthetic lumen against the surrounding endolithium of the body lumen system beyond the aneurysm. The specific structures of these locally optimized prostheses are more fully explained in co-pending U.S. patent application Ser. No. 08/615,697, filed Mar. 13, 1996 (Attorney Docket No. 16380-004100), the full disclosure of which has previously been incorporated by reference.

Advantageously, bifurcated prosthesis 60 is generally assembled in situ by first expanding trunk portion 64, separation portion 62, and one of the branch portions 68 within the aorta and one of the iliac arteries. The second branch portion 68 is then expanded within the open branch port 72 of separation portion 62, thereby allowing the aneurysm to be isolated by trunk sealing cuff 66 and branch sealing cuffs 70.

Figure 4A:
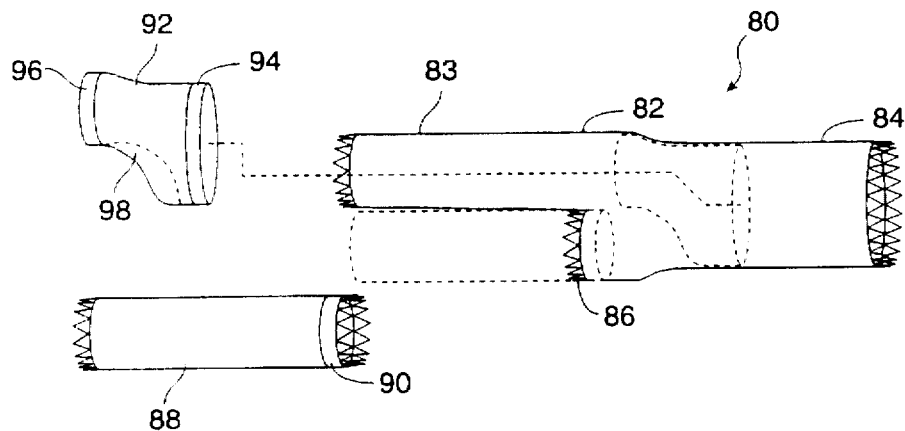
FIG. 4A illustrates a bifurcated endoluminal prosthetic system which includes a bifurcated endoluminal prosthesis, a branch prosthesis, and a shunt for deployment within the bifurcated prosthesis, the shunt for use if deployment of the branch prosthesis proves impracticable or ineffective.

An endoluminal prosthesis system 80 is schematically illustrated in FIG. 4A. A bifurcated prosthesis 82 includes a trunk portion 84, a branch portion 83, and an open second branch port 86. When possible, it is generally preferable to completely deploy branch prosthesis 88 by radially expanding end 90 within branch port 86 so that the branch prosthesis provides a direct prosthetic lumen from the aorta to the healthy portion of the adjacent iliac. However, where direct connection of the aorta and iliac are not feasible, the present system further provides a shunt 92 having a trunk sealing end 94 and a branch sealing end 96. When required, the shunt can be radially expanded within the bifurcated prothesis so as to seal off branch port 86. Generally, shunt 92 will include a membrane 98 which is substantially impermeable, so that the shunt provides an effective seal or barrier against fluid communication with branch port 86, and so that the shunt re-directs the lumenal flow.

Figure 4B:
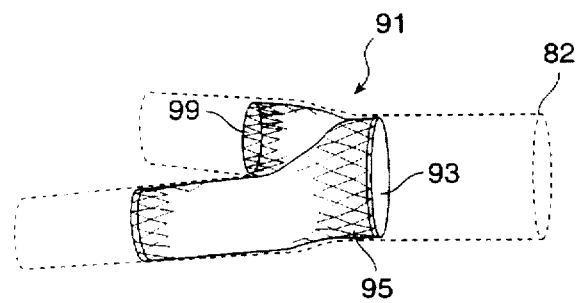
FIG. 4B illustrates a shunt for deployment within a bifurcated prosthesis, wherein the shunt comprises a liner supported by a frame having a trunk portion, a branch portion, and a branch port portion so that the frame is highly stable when the shunt is expanded within the bifurcated prosthesis.

A particularly stable shunt structure 91 is illustrated in FIG. 4B. Stable shunt 91 comprises a liner 93 supported by a perforate, radially expandable frame having a trunk portion 95, a branch portion 97, and a branch port portion 99. When deployed, the frame expands within the prosthetic lumenal intersection of bifurcated prosthesis 84 as shown. The shunt's port portion 99 helps ensure that the position will be highly stable, and that there is little possibility that the shunt will move inadvertently. Preferably, the liner tapers smoothly from the trunk portion to the branch portion to minimize stagnation zones which could otherwise promote the formation of thrombus.

Figure 5A:
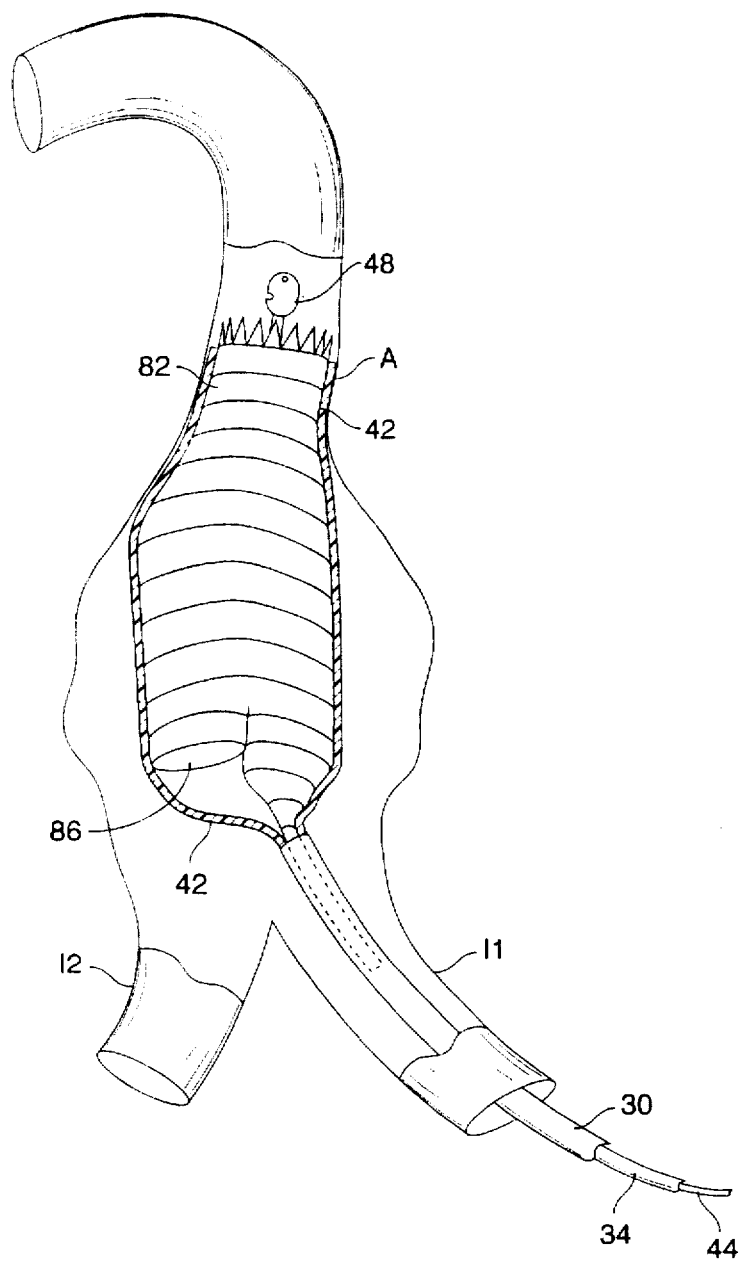
FIGS. 5A & B illustrate the deployment of a bifurcated endoluminal prosthesis to provide therapy for an abdominal aortic aneurysm when both iliac arteries are accessible.

The deployment of bifurcated prosthesis 82, including the in situ assembly of branch prosthesis 88, is seen most clearly in FIGS. 5A and B. Generally, the bifurcated prosthesis is radially compressed within delivery catheter 30, and the delivery catheter is introduced into the vascular system, typically using either a percutaneous or cut-down procedure. Bifurcated prosthesis 82 is positioned across an abdominal aortic aneurysm AA so that the trunk portion 84 extends into the aorta A, while the branch portion extends into a first iliac I1. Preferably, branch port 86 is radially oriented toward the alternate iliac I2, generally under the guidance of fluoroscopy and/or intravascular ultrasound (IVUS), and with the assistance of asymmetric markings on nosecone 48, markings on the prosthesis itself, and the like.

Once the compressed bifurcated prosthesis is properly positioned, deployment begins by retracting the outer sheath of catheter 30 while maintaining the position of shaft 34. Runners 42 flex outward with the expanding prosthesis as shown. Once the prosthesis is fully released, the axial runners can be withdrawn into the sheath of the catheter, and the catheter can be withdrawn.

Figure 5B:
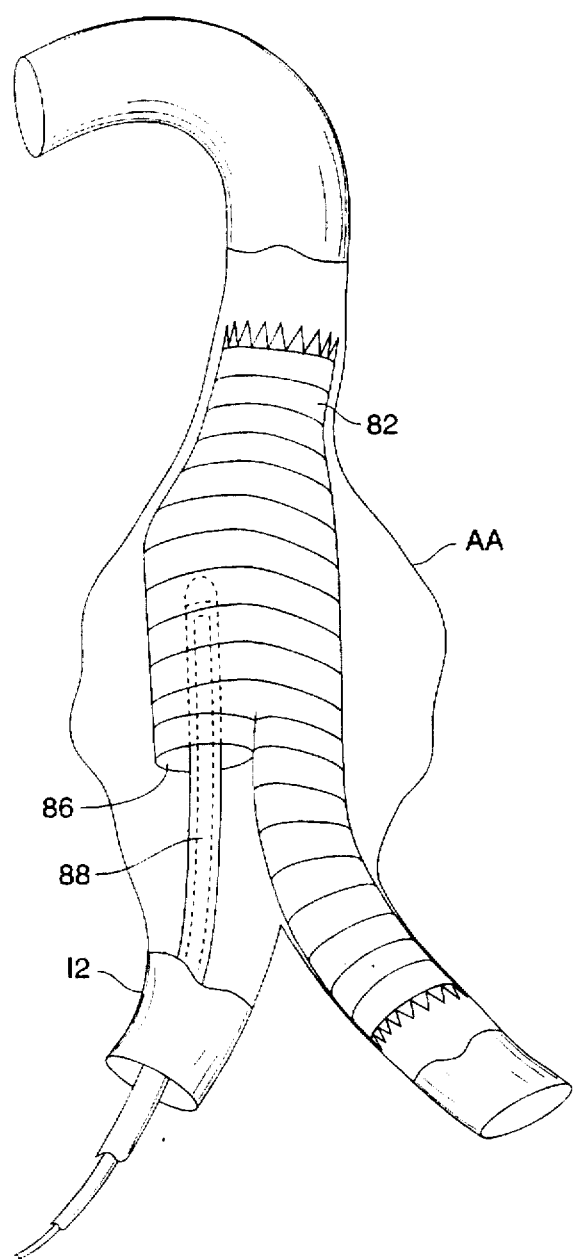

If all goes well, branch prosthesis 88 may be positioned so that it extends from branch port 86 to alternate iliac I2, as shown in FIG. 5B. The branch prosthesis may then be expanded into sealing engagement with the bifurcated prosthesis to complete the deployment of the bifurcated prosthetic system. Advantageously, the prosthetic lumen of this completed system provides a direct, smooth flow of blood to each of the first and second iliac I1, I2, without straining the weakened vascular wall forming the abdominal aortic aneurysm AA.

Figure 6:
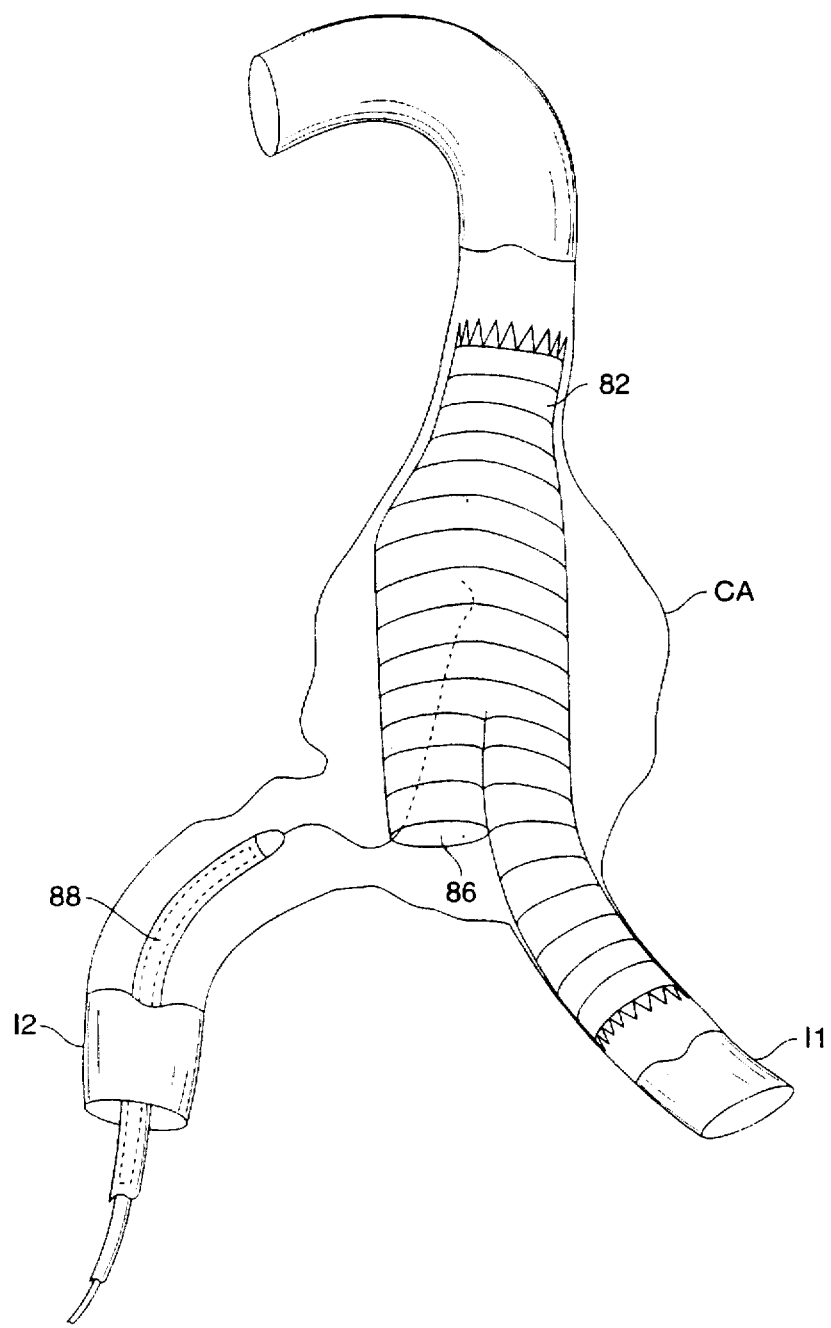
FIG. 6 illustrates an abdominal aortic aneurysm having a geometry which complicates deployment of the branch prosthesis between the branch port of the bifurcated prosthesis and the second of the two iliac arteries.

Unfortunately, not all diseased vascular geometries provide such easy access for completion of the bifurcated prosthetic system. As illustrated in FIG. 6, a highly convoluted aneurysm CA has distorted the aortoiliac junction so that completion of the bifurcated prosthetic system is not feasible. In fact, even if it were possible to position the delivery catheter from the bifurcated prosthesis to the alternate iliac I2, expansion of the branch prosthesis across this acute angle may well strain the convoluted aneurysm so as to cause a rupture, or may release the loose thrombus from within the aneurysm to the surrounding blood stream.

Such situations may arise from a variety of causes, including folds in the aneurysm which were not clearly visible under imaging, from inaccurately positioned bifurcated prostheses, and the like. Alternatively, thrombus may have accumulated in connection with the aneurysm, or the iliaci may by occluded by plaque or the like. In the advanced stages, aneurysms may lead to extreme tortuosity of the iliac so as to prevent passage of the guidewire and/or catheter, or tortuosity of the aorta upstream of the aneurysm may prevent alignment of the branch port with the iliac. A preferred method for using shunt 92 to overcome such situations will be explained with reference to FIGS. 7A–D.

Shunt 92 is also introduced into the vascular system compressed within a delivery catheter, as described above. Shunt 92 is positioned within bifurcated prosthesis 82 (shown in FIGS. 7A–8 in a partial cut away view) so that the shunt extends from the trunk portion 84 to the branch portion 83. The shunt is then expanded, typically by withdrawing a sheath of the delivery catheter while holding the axial position of the shunt, as was also described above.

Figure 7A:
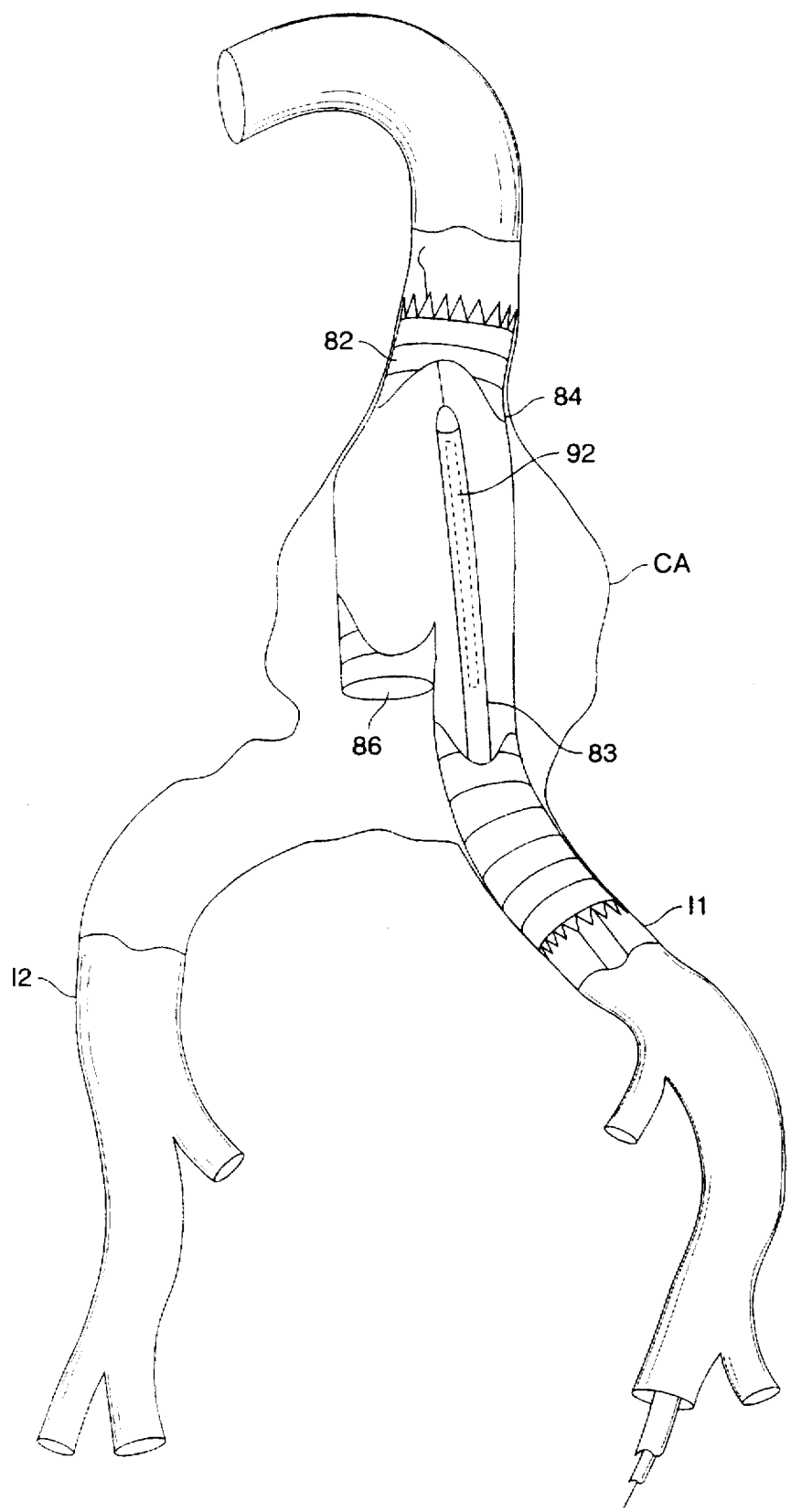
FIGS. 7A–D illustrate a method for deploying a shunt within a bifurcated endoluminal prosthesis to effectively provide a single-lumen prosthetic therapy, a portion of the bifurcated prosthesis being broken away to show deployment of the shunt therein, and also shows a femorofemoral bypass and occlusion of one iliac artery with detachable balloons so as to isolate an abdominal aortic aneurysm, according to the principles of the present invention.
Figure 7B:
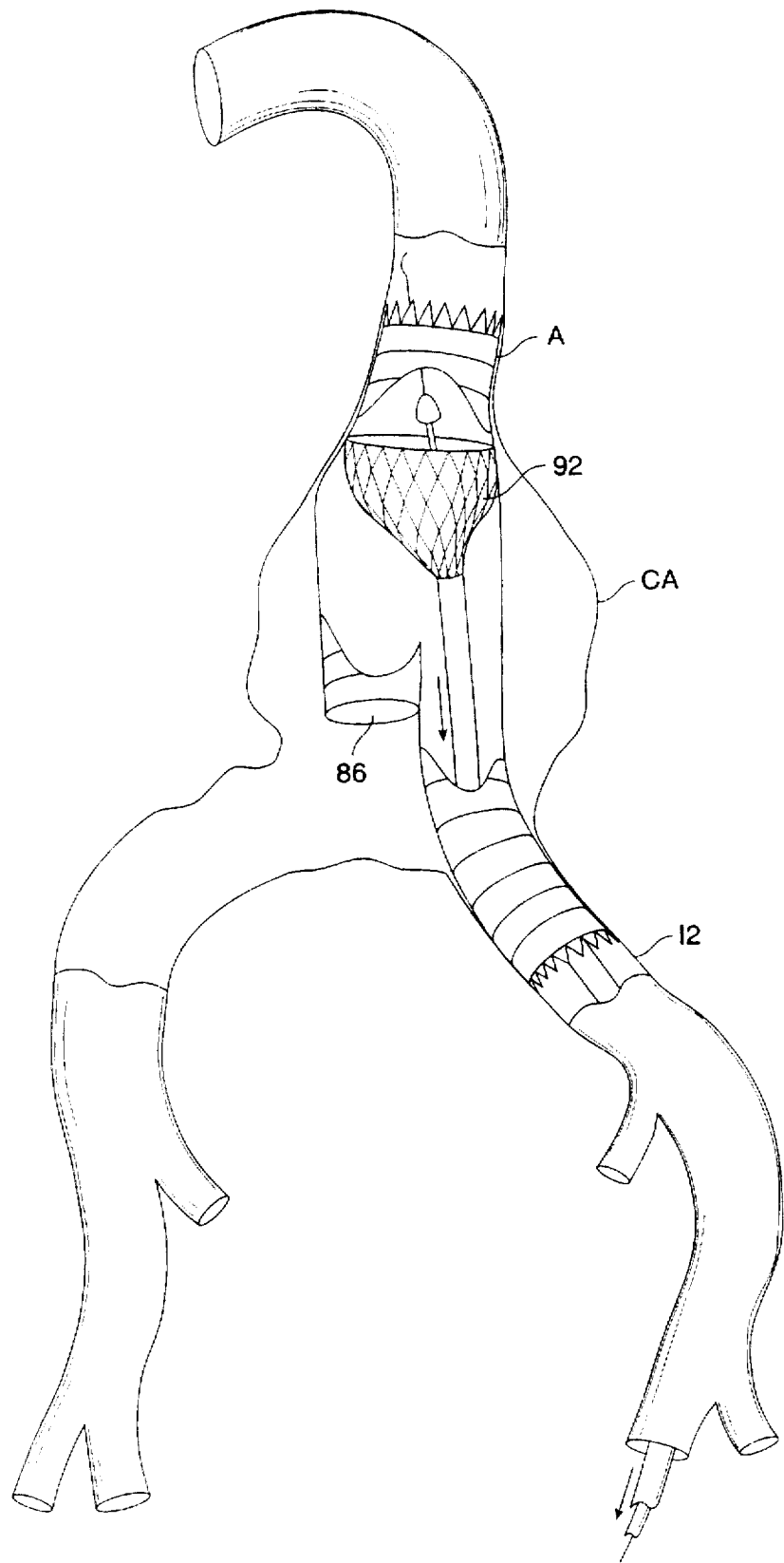
Figure 7C:
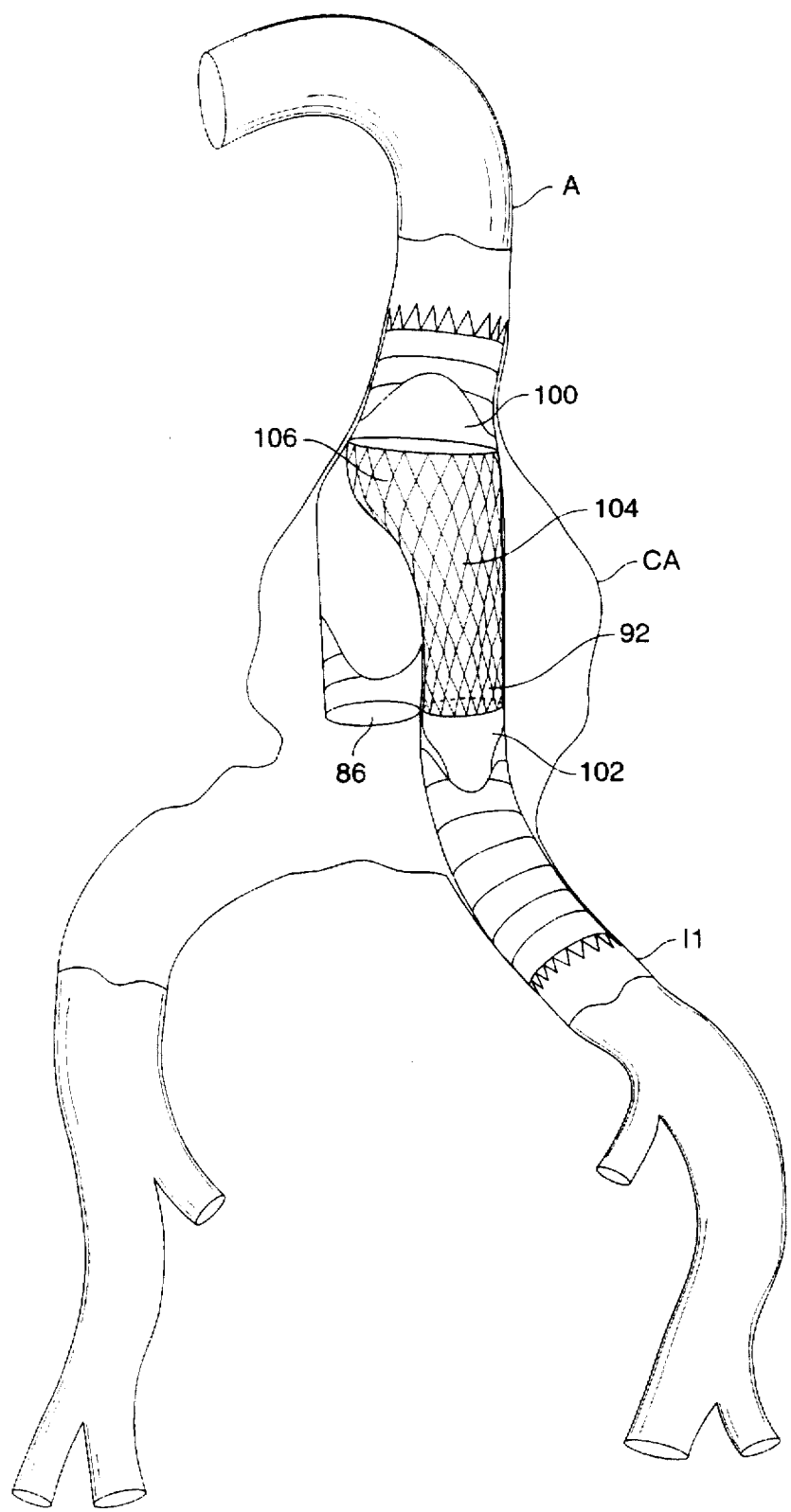
Figure 7D:
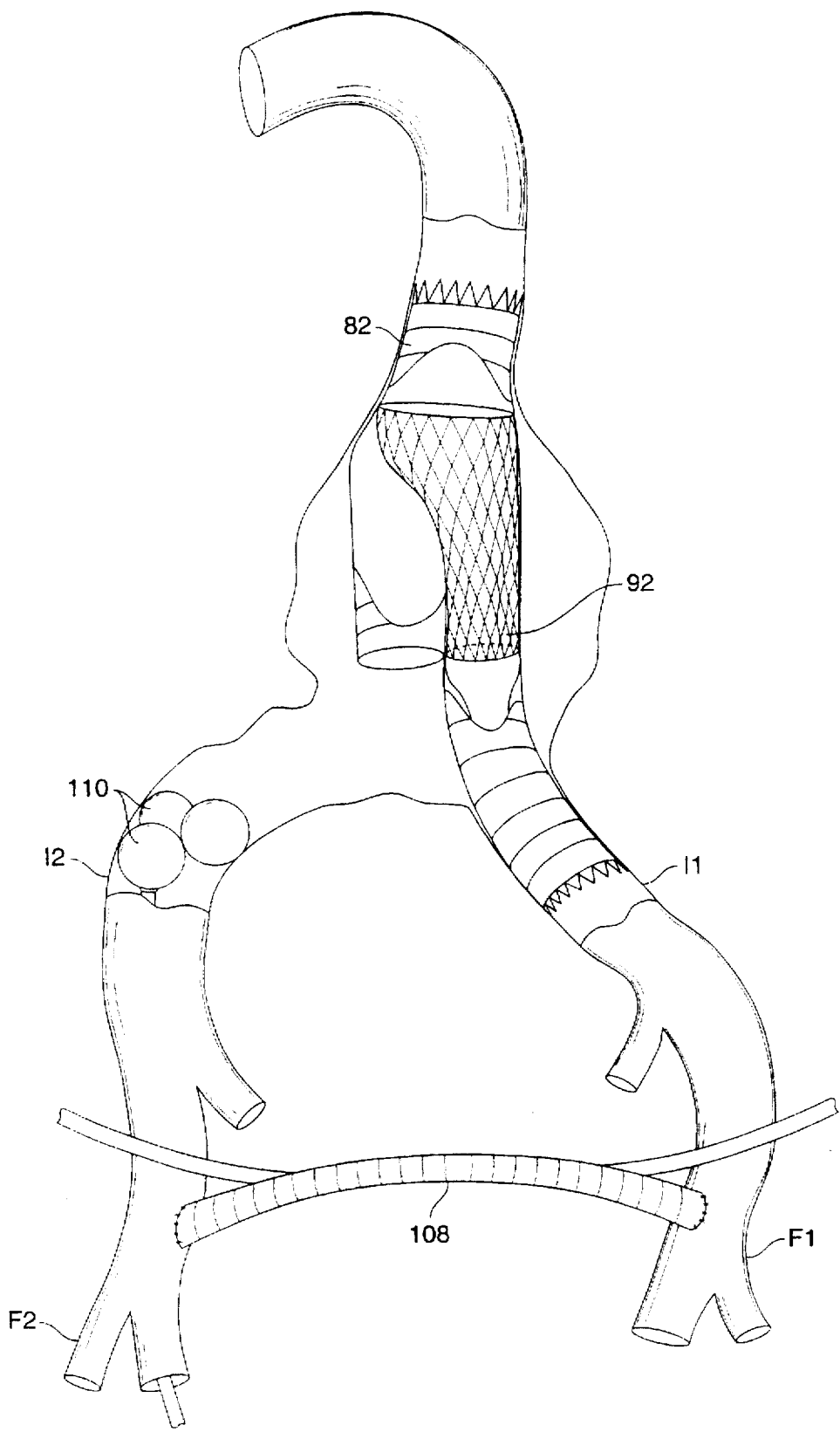

As shunt 92 expands, it engages the surrounding lumen of the bifurcated prosthesis, typically sealing against a trunk lumen 100 within the trunk portion, and against a branch lumen 102 within the branch portion. As the bifurcated prosthesis is generally sealed against the aorta and first iliac, sealing off of branch port 86 with shunt 92 will generally isolate the convoluted artery CA from the direct pressure from blood flow therethrough, as illustrated in FIG. 7C. Ideally, the shunt will also provide a smoothly tapering prosthetic lumen to minimize the strain on the heart, and to avoid areas of blood stagnation which might otherwise lead to the formation of thrombus.

The structure of shunt 92 is typically similar to other tubular endoluminal prostheses, ideally comprising an external perforated frame 104 supporting a substantially impermeable liner 106. The ends of the shunt may include sealing cuffs comparable to those described above. Often times, the frame will expand resiliently against the surrounding bifurcated prosthetic lumen, and may include barbs or other protruding structures to firmly affix the position of the shunt against the surrounding bifurcated prosthesis. Advantageously, there is little risk of injury to the tissue itself, which may be at some distance from this prosthetic lumen.

The liner may comprise a woven polyester such as Dacron™, or may alternatively include partially oriented yarn, PTFE, or some other radially expansible material, as more fully explained in co-pending U.S. patent application Ser. No. 08/595,944, filed Feb. 6, 1996 (Attorney Docket No. 16380-004010) the full disclosure of which is incorporated herein by reference. Alternatively, shunt 92 may comprise a malleable structure and be plastically expanded in place with a mechanical expansion device such as a balloon catheter or the like.

Once shunt 92 has been deployed within bifurcated prosthesis 82, an alternative path for blood to alternate iliac I2 will often be provided, typically using a femorofemoral bypass technique, as is generally known in the art. Such techniques generally rely on a vascular bypass graft 108 to supply blood from a first femoral artery F1 to the alternate femoral artery F2. The aneurysm is generally fully isolated by occluding alternate iliac I2 with detachable balloons 110 or some other occlusion device.

Figure 8A:
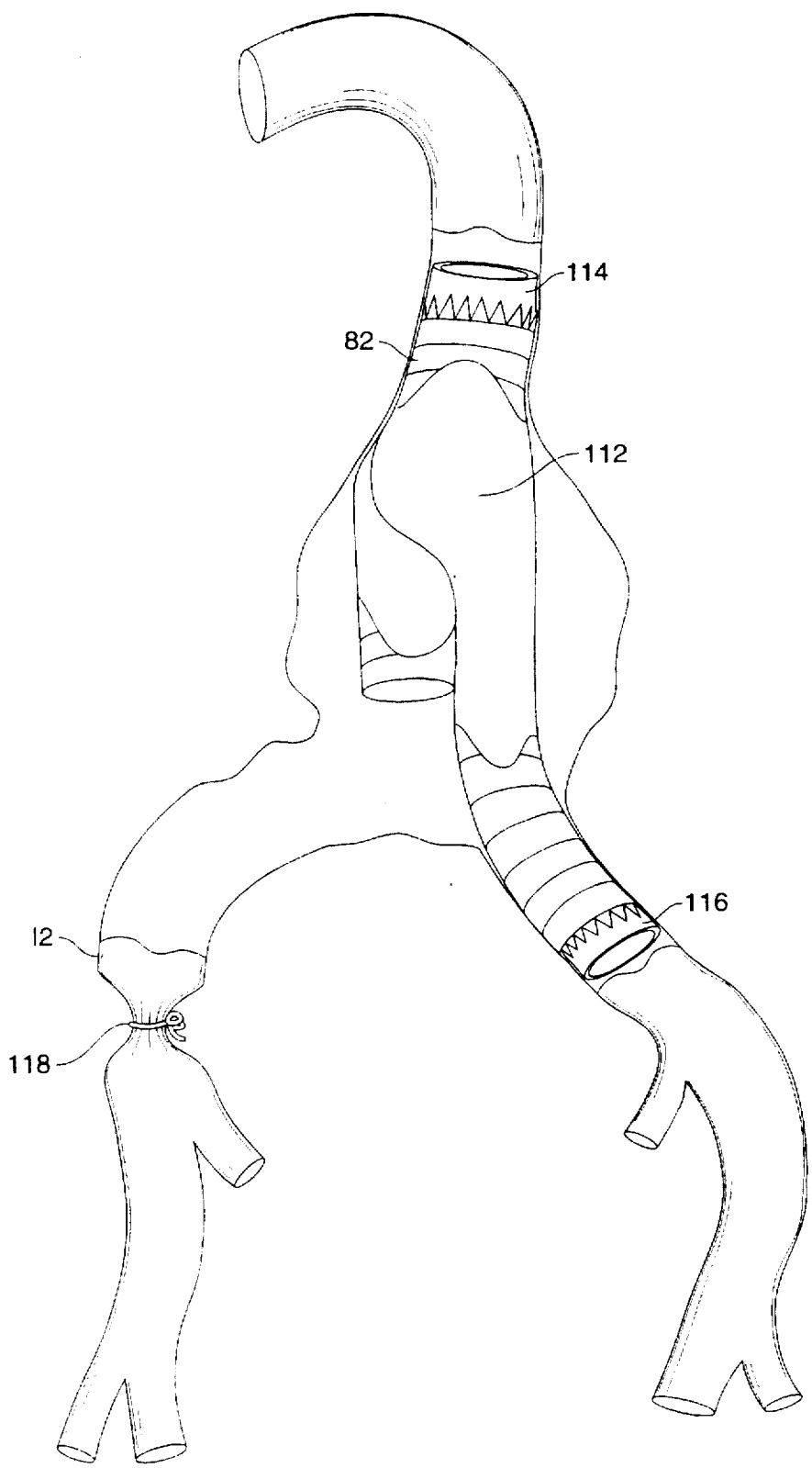
FIG. 8A illustrates an alternative method for occluding the port of a bifurcated endoluminal prosthesis by deploying a self supporting tubular body within the bifurcated prosthesis, and by ligating one of the iliac arteries.

Clearly, a wide variety of shunt structures may be provided. For example, as illustrated in FIG. 8A, a conformable self-supporting polymeric shunt having a structure similar to that described in co-pending U.S. patent application Ser. No. 08/595,944, filed Feb. 6, 1996 (Attorney Docket No. 16380-004010), may rely in part on the surrounding bifurcated prosthetic structure 82, and provides a soft conformable seal against the body lumen at its upstream and downstream ends 114, 116. Additionally, the alternative iliac can be occluded using ligation sutures 118, as will be recognized by those of skill in the art.

Figure 8B:
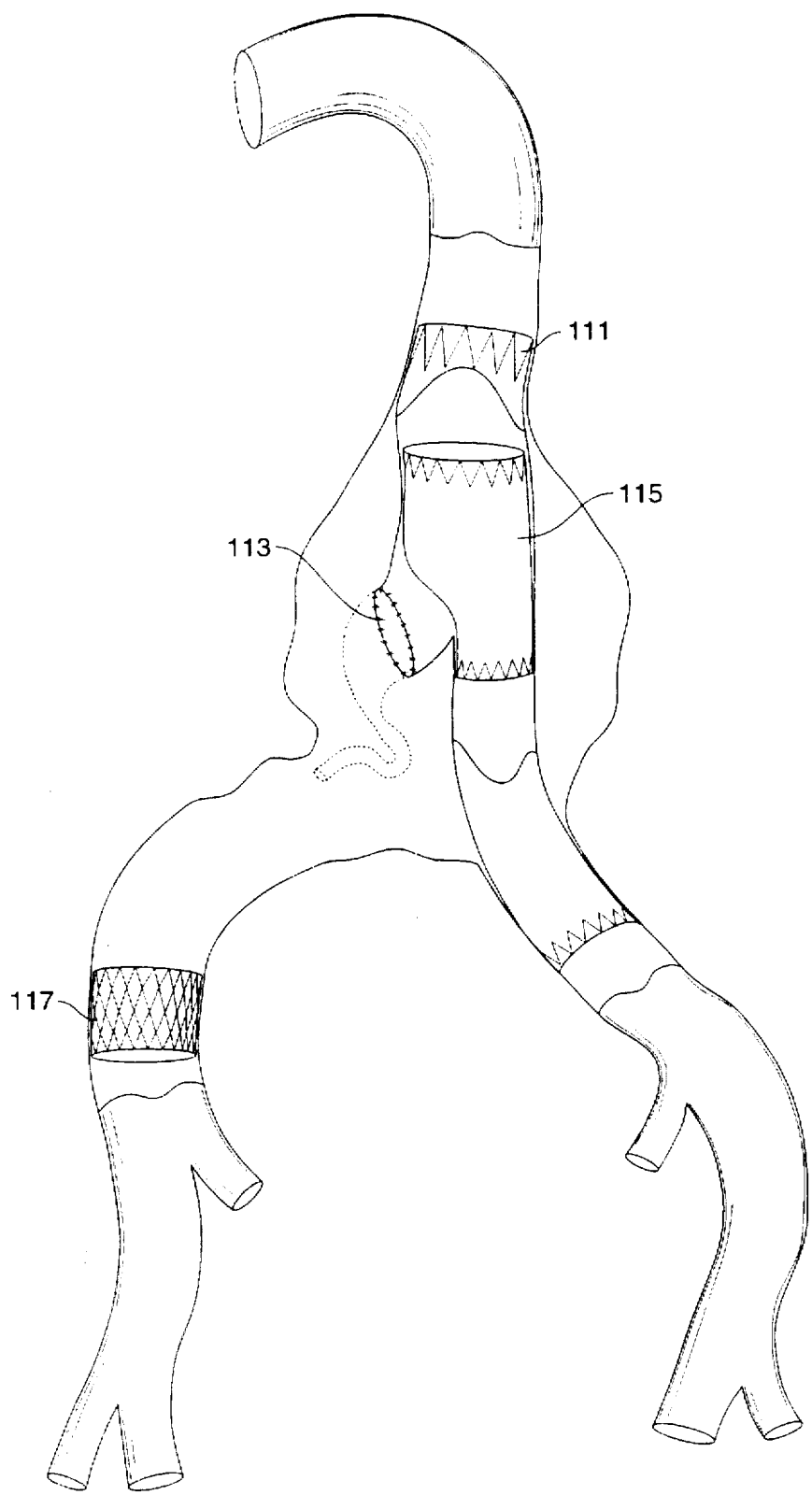
FIGS. 8B–D illustrate still further alternative methods for occluding the branch port of a bifurcated endoluminal prosthesis, according to the principles of the present invention.
Figure 8C:
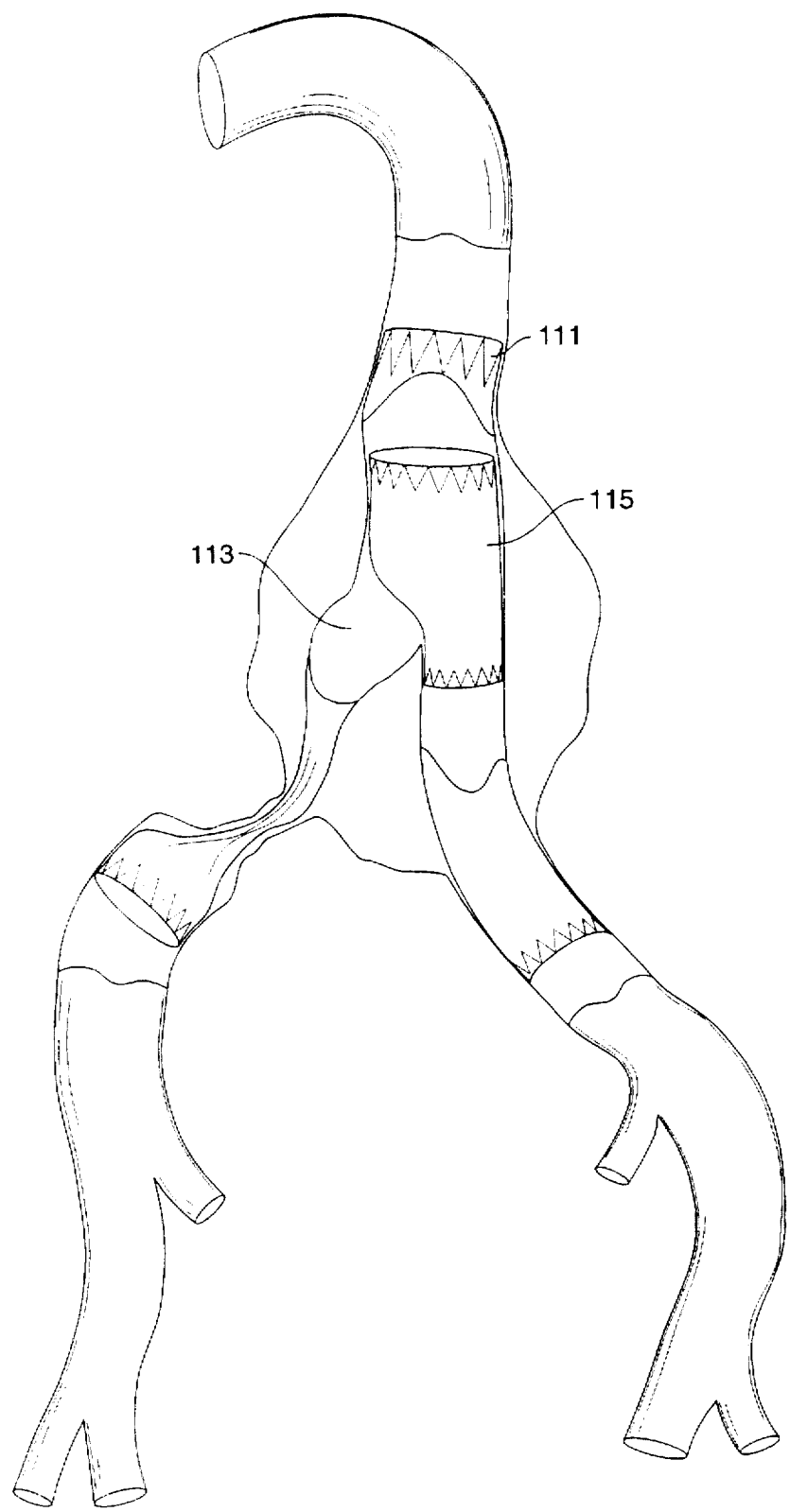
Figure 8D:
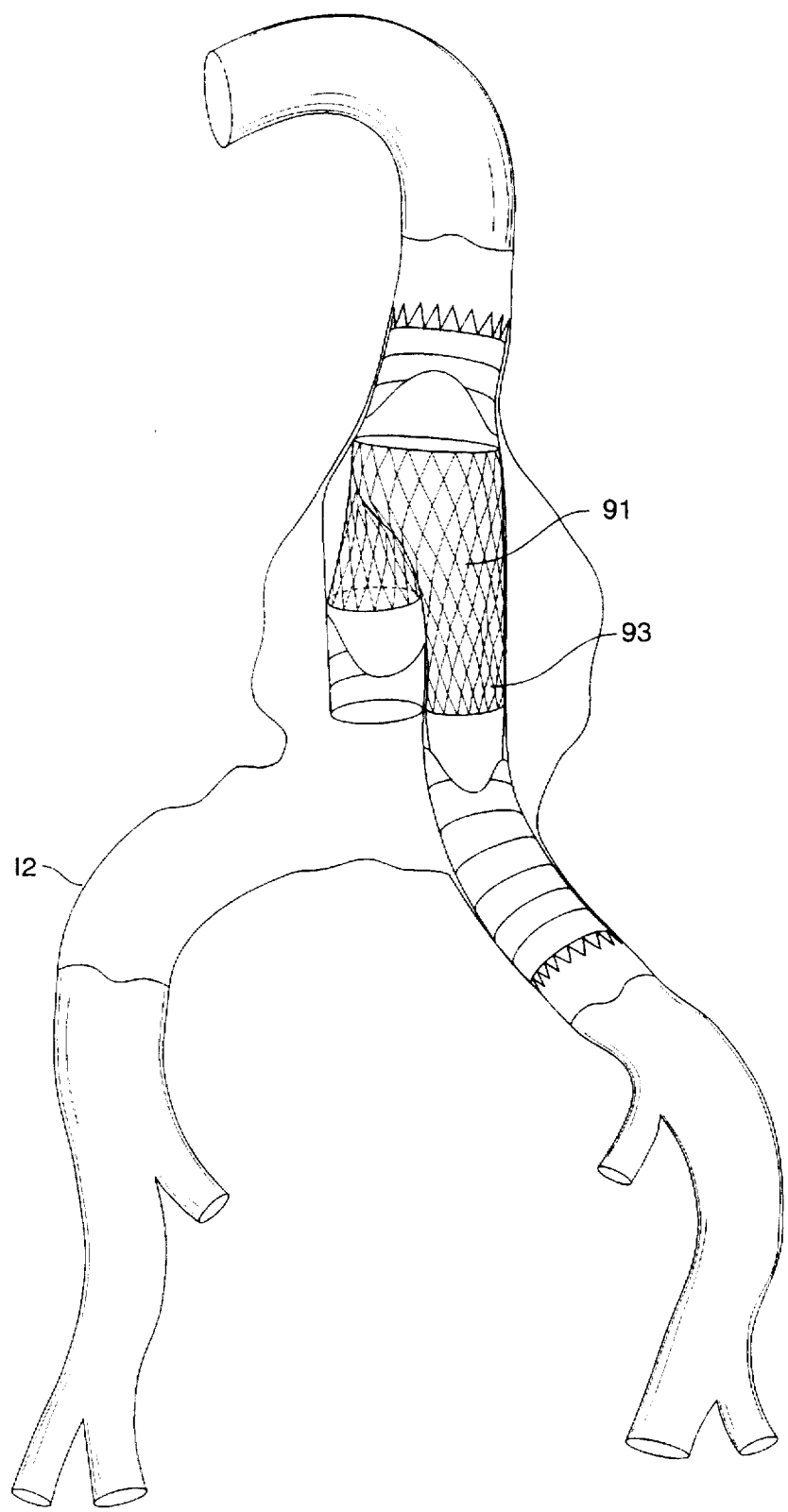
Figure 9:
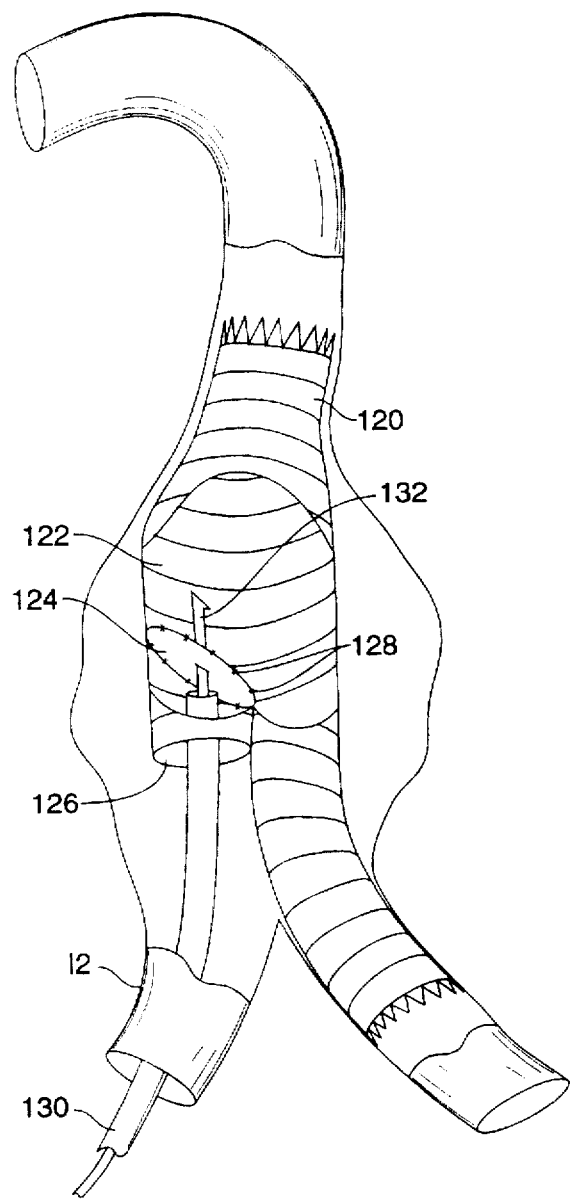
FIG. 9 illustrates an alternative single-lumen/bifurcated prosthetic structure and method, in which a port of the bifurcated prosthesis is initially sealed by a membrane when the bifurcated prosthesis is deployed, and in which the membrane is removed and/or opened when the branch port proves to be accessible for deployment of a branch prosthesis therein.

Still further embodiments of devices and methods according to the present invention are illustrated in FIGS. 8B–D. Complete deployment of an integral bifurcated endoluminal prosthesis 111 may be prevented by occlusive plaque within the iliac, by tortuosity from an advanced aneurysm, or the like. Even where nominally complete positioning is accomplished, such occlusion may prevent the bifurcated prosthetic lumen system from providing an adequate blood-flow to each branch, particularly where an axial portion of the prosthesis is formed by a liner which is not radially supported by the frame, as shown in FIG. 8C. By deploying a shunt within integral prosthesis 111, an integral branch port 113 is isolated from the lumenal flow.

Optionally, the unused portion of the integral prosthesis may be detached and removed transluminally, as shown schematically in FIG. 8B. Also shown is an optional two-ringed shunt 115, which includes a tubular liner supported at either end in sealing engagement against the surrounding bifurcated prosthesis by radially expandable ring frames, thereby minimizing frame size and the volume required for the compressed shunt structure. An alternative occlusion device 117 comprises a liner supported by a radially expandable frame, wherein the liner covers at least one end to substantially isolate the aneurysm from the femoral artery.

The deployed positional stability of stable shunt 91 can be understood with reference to FIG. 8D, which shows the branch port portion of the shunt frame. This frame structure helps to affix the shunt at the lumenal intersection. The upstream and downstream ends of the liner seal against the surrounding prosthetic lumen, the liner optionally being sewn to the end of the frame, folded over the end of the frame, or the like. Additionally, in this embodiment of the present method, the bifurcated prosthesis adjacent the branch port engages the second iliac to help isolate the aneurysm.

In a still further alternative, a bifurcated prosthesis 120 includes a prosthetic lumen 122 which is initially isolated from a branch port 126 by a removable membrane 124. Membrane 124 is releasably secured to the prosthesis using frangible sutures 128. This allows alternative bifurcated prosthesis 120 to be used as either a bifurcated or single-lumen prosthesis, as removable membrane 124 can be removed once it has been found that branch port 126 is accessible for deployment of a branch prosthesis between the alternate iliac I2 the branch port. Removal is shown here using a barbed tool 132 positioned through a removal catheter 130. Alternatively, the membrane could be dilated, dissolved, or otherwise opened to allow fluid communication using a wide variety of structures.

Although the foregoing invention has been described in some detail, by way of illustration and example, for purposes of clarity of understanding, certain changes and modifications will be obvious to those of skill in the art.

Therefore, the scope of the present invention is limited solely by the scope of the appended claims.

What is claimed is:

1. A method for repairing a bifurcated body lumen system having a trunk lumen in fluid communication with first and second branch lumens at a lumenal intersection, wherein a tubular bifurcated endoluminal prosthesis is deployed within the body lumen system so that a trunk portion of the prosthesis extends into the trunk lumen and a first branch portion of the prosthesis extends into the first branch lumen, and wherein a second branch port of the prosthesis is disposed between the trunk and branch portions, the method comprising substantially sealing the second branch port of the prosthesis to prevent fluid communication between the prosthetic trunk lumen and the body lumen system through the second branch port.

2. A method as claimed in claim 1, further comprising providing a passage for fluid communication between the first branch lumen and the second branch lumen of the body lumen system.

3. A method as claimed in claim 1, wherein the sealing step comprises deploying a shunt within the bifurcated prosthesis so that the shunt extends from the trunk portion to the branch portion, and so that a membrane of the shunt substantially blocks fluid communication between the prosthetic trunk lumen and the second branch port of the bifurcated prosthesis.

4. A method as claimed in claim 3, further comprising sealingly engaging the membrane against the prosthetic trunk lumen, the membrane comprising a tubular liner.

5. A method as claimed in claim 3, further comprising sealingly engaging the membrane against a prosthetic first branch lumen within the branch portion of the bifurcated prosthesis.

6. A method as claimed in claim 3, further comprising sealingly engaging the membrane directly against at least one of the trunk lumen of the body lumen system and the branch lumen of the body lumen system, the shunt extending axially beyond at least one of the branch portion and the trunk portion of the bifurcated prosthesis.

7. A method as claimed in claim 3, further comprising deploying the shunt with a cross-section which transitions smoothly between a trunk cross-section of the prosthetic trunk lumen and a branch cross-section of a prosthetic branch lumen of the branch portion.

8. A method for repairing an aneurysm of an abdominal aortic artery adjacent first and second iliac arteries, the method comprising:

deploying a bifurcated tubular endoluminal prosthesis within the aneurysm so that a trunk portion of the prosthesis having a trunk lumen extends into the aorta and a first branch portion of the prosthesis having a first branch lumen extends into the first iliac, wherein a second branch port of the prosthesis is disposed between the trunk and branch portions;

deploying a shunt within the bifurcated prosthesis so that the shunt extends from the trunk lumen to the branch lumen, and so that the shunt substantially blocks fluid communication between the prosthetic trunk lumen and the second branch port of the bifurcated prosthesis.

9. A method as claimed in claim 8, further comprising determining that the second branch port of the bifurcated prosthesis is substantially inaccessible for deployment of a second tubular branch endoluminal prosthesis extending from the second branch port into the second iliac before deploying the shunt.

10. A method as claimed in claim 8, further comprising providing a femorofemoral bypass so as to allow blood flow from a first femoral artery adjacent the first iliac to a second femoral artery adjacent the second iliac.

11. A method as claimed in claim 8, further comprising occluding the second iliac between the aneurysm and the femorofemoral bypass so as to prevent blood from flowing back through the second iliac into the aneurysm.

12. A method for repairing an aneurysm of an abdominal aortic artery adjacent first and second iliac arteries, after deploying a bifurcated endoluminal prosthesis within the aneurysm so that a trunk portion of the prosthesis extends into the aorta and a first branch portion of the prosthesis extends into the first iliac, wherein a second branch port of the prosthesis is disposed between the trunk and branch portions, and wherein the second branch port of the bifurcated prosthesis is inaccessible for deployment of a tubular second branch endoluminal prosthesis therein, the method comprising:

deploying a shunt within the bifurcated prosthesis so that the shunt extends from the trunk portion to the branch portion of the bifurcated prosthesis, and so that the shunt substantially blocks blood flow from the prosthetic trunk lumen to the second branch port of the bifurcated prosthesis, wherein the shunt does not substantially occlude blood flow between the trunk lumen and the branch lumen of the bifurcated prosthesis.

* * * * *